United States Patent
Muraoka et al.

(10) Patent No.: US 11,801,027 B2
(45) Date of Patent: Oct. 31, 2023

(54) STORAGE MEDIUM, DYNAMIC ANALYSIS APPARATUS, AND DIAGNOSIS SUPPORTING SYSTEM

(71) Applicant: Konica Minolta, Inc., Tokyo (JP)

(72) Inventors: Taketoh Muraoka, Hino (JP); Takenori Fukumoto, Kamakura (JP)

(73) Assignee: KONICA MINOLTA, INC., Tokyo (JP)

( * ) Notice: Subject to any disclaimer, the term of this patent is extended or adjusted under 35 U.S.C. 154(b) by 284 days.

(21) Appl. No.: 17/206,770

(22) Filed: Mar. 19, 2021

(65) Prior Publication Data

US 2021/0290192 A1    Sep. 23, 2021

(30) Foreign Application Priority Data

Mar. 23, 2020   (JP) .................................. 2020-050421

(51) Int. Cl.
*A61B 6/00* (2006.01)
*G06T 7/00* (2017.01)
*G16H 50/30* (2018.01)

(52) U.S. Cl.
CPC ............ *A61B 6/5217* (2013.01); *A61B 6/461* (2013.01); *G06T 7/0012* (2013.01); *G16H 50/30* (2018.01); *G06T 2207/10* (2013.01); *G06T 2207/30061* (2013.01)

(58) Field of Classification Search
CPC ....... A61B 6/5217; A61B 6/461; A61B 5/085; A61B 5/1135; A61B 6/50; A61B 6/48; A61B 5/0816; A61B 5/091; G06T 7/0012; G06T 2207/10; G06T 2207/30061; G06T 7/0016; G16H 50/30; G16H 30/40
See application file for complete search history.

(56) References Cited

U.S. PATENT DOCUMENTS

2012/0041279 A1* 2/2012 Freeman .............. A61B 5/0535
                                                 600/534
2012/0101400 A1* 4/2012 Kurosawa ............ A61B 5/0809
                                                 600/533

FOREIGN PATENT DOCUMENTS

JP        2019-187862 A     10/2019

* cited by examiner

*Primary Examiner* — Siamak Harandi
(74) *Attorney, Agent, or Firm* — LUCAS & MERCANTI, LLP

(57) ABSTRACT

A non-transitory computer-readable storage medium storing a program causing a computer to perform the following, obtaining a radiation moving image in which a chest portion of a subject when the subject breathes is shown; analyzing a dynamic state of the chest portion based on the radiation moving image obtained in the obtaining; and extracting impedance regarding breathing based on an analysis result obtained in the analyzing.

13 Claims, 3 Drawing Sheets

STORAGE MEDIUM, DYNAMIC ANALYSIS APPARATUS, AND DIAGNOSIS SUPPORTING SYSTEM

CROSS-REFERENCE TO RELATED APPLICATIONS

The entire disclosure of Japanese Patent Application No 2020-050421 filed on Mar. 23, 2020 is incorporated herein by reference in its entirety.

BACKGROUND

Technological Field

The present invention relates to a storage medium, a dynamic analysis apparatus, and a diagnosis supporting system.

Description of the Related Art

Conventionally, diagnosis of the respiratory function is performed by the following procedure. In a respiratory examination performed in advance, the subject performs forced breathing (for example, breathe out or breathe in to a point that it is not possible to breathe out or breathe in any more, breathe out or breathe in as much as possible within a predetermined amount of time, or the like). The value which can be calculated from the expiratory amount and the inspiratory amount measured above is used as the index in the diagnosis of the respiratory function.

Lately, in such respiratory examination, instead of measuring the expiratory amount or the inspiratory amount using examination tools (for example, spirometer), the following technique is proposed. That is, a chest portion of the subject when the subject is breathing is imaged by radiation and the obtained radiation moving image is analyzed. With this, a numeric value which is to be an index is estimated.

For example, JP 2019-187862 describes a radiation image analysis apparatus which is configured to calculate an area of a lung field from a chest portion image obtained by imaging the chest portion with radiation from one direction and which estimates a residual volume of a lung field, a functional residual capacity, a total lung capacity or a residual rate based on the calculated area of the lung field.

SUMMARY

Even if the subject himself believes he is breathing out or breathing in the same amount as usual, the amount of air breathed out or breathed in by the subject may change depending on a physical or mental state of the subject at that time. Therefore, even if the subject is making an effort to perform forced breathing, the technician performing the respiratory examination cannot objectively determine whether breathing which is sufficient for obtaining an accurate index is being performed. As a result, the obtained index may lack in reliability.

Moreover, the technician making an intervention to urge the subject to make an effort leads to an increase in the burden of performing the respiratory examination for the technician.

On the other hand, even if the subject is making an effort to perform forced breathing, when the technician determines that the breathing is not enough and the technician makes a request to the subject to make a better effort, the subject needs to breathe harder. Such a situation is only a pain both mentally and physically to the subject.

Moreover, it is a heavy physical burden to the subject to perform forced breathing soon after an operation (for example, during a rehabilitation term). Therefore, to the subject soon after the operation, it is difficult to perform a respiratory examination.

The present invention is made in view of the above problems, and the object of the present invention is to be able to obtain an index in order to perform a diagnosis of a respiratory function without forced breathing by the subject.

To achieve at least one of the abovementioned objects, according to an aspect of the present invention, reflecting one aspect of the present invention, a non-transitory computer-readable storage medium storing a program causing a computer to perform: obtaining a radiation moving image in which a chest portion of a subject when the subject breathes is shown; analyzing a dynamic state of the chest portion based on the radiation moving image obtained in the obtaining; and extracting impedance regarding breathing based on an analysis result obtained in the analyzing.

According to another aspect, a non-transitory computer-readable storage medium storing a program causing a computer to perform: obtaining of a radiation moving image in which a chest portion is shown when a predetermined amount of air is breathed out or breathed in; analyzing a dynamic state of the chest portion based on the obtained radiation moving image; based on an analysis result obtained in the analyzing, extracting a density, area or position of a target site included in the chest portion or a change amount of the density, a change amount of the area or a change amount of the position.

According to another aspect, a dynamic analysis apparatus including: a hardware processor, wherein the hardware processor is configured to perform, obtaining a radiation moving image in which a chest portion of a subject when the subject breathes is shown, analyzing a dynamic state of the chest portion based on the radiation moving image obtained in the obtaining, and extracting impedance regarding breathing based on an analysis result obtained in the analyzing.

A diagnosis supporting system including: a detector which generates a radiation moving image in which a chest portion of a subject when the subject breathes is imaged; and a dynamic analysis apparatus, wherein the dynamic analysis apparatus is configured to perform, analyzing a dynamic state of the chest portion based on the radiation moving image generated by the detector; and extracting impedance regarding breathing based on an analysis result obtained in the analyzing.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

First Embodiment

Hereinafter, one or more embodiments of the present invention will be described with reference to the drawings. However, the scope of the invention is not limited to the disclosed embodiments and drawings.

The first embodiment is described in detail with reference to the drawings.

[1. Diagnosis Supporting System]

First, a schematic configuration of a diagnosis supporting system (hereinafter, system 100) according to the present embodiment is described.

Figure 1:
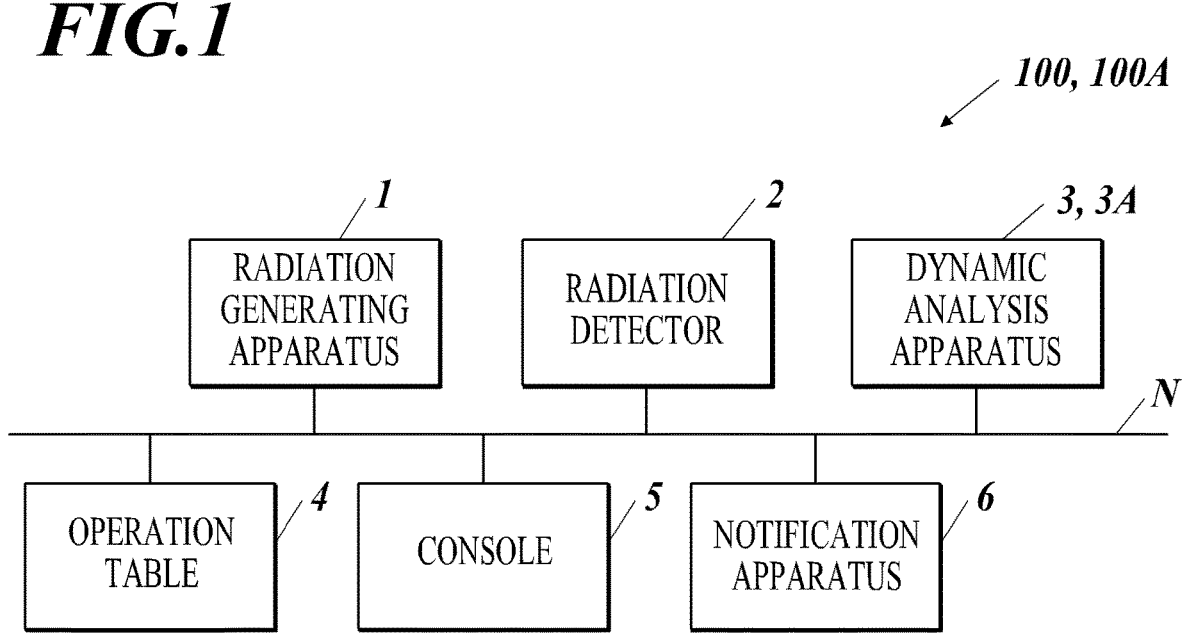
FIG. 1 is a block diagram showing a diagnosis supporting system according to an embodiment of the invention.

FIG. 1 is a block diagram showing the system 100.

Reference numerals 3A and 100A in FIG. 1 show the numerals for the second embodiment described later.

(Configuration of Diagnosis Supporting System)

The system 100 is used when a technician performs a respiratory examination (imaging of a radiation moving image). The system 100 is also used in order to provide an index when a doctor performs diagnosis of a respiratory function.

As shown in FIG. 1, the system 100 includes a radiation generating apparatus (hereinafter referred to as generating apparatus 1), a radiation detector (hereinafter referred to as detector 2), and a dynamic analysis apparatus (hereinafter referred to as analysis apparatus 3).

The system 100 according to the present embodiment further includes an operation table 4, a console 5, and a notification apparatus 6.

The apparatuses 1 to 6 are able to communicate with each other through a communication network N (LAN (Local Area Network), WAN (Wide Area Network), internet, etc.).

The system 100 may be configured to be able to communicate with a Hospital Information System (HIS), a Radiology Information System (RIS), a Picture Archiving and Communication System (PACS), or the like which are not illustrated.

Radiation Generating Apparatus

The generating apparatus 1 includes a high voltage generator, a vacuum tube or the like which are not shown.

Based on a control signal input from an operation table 4, the high voltage generator applies to the vacuum tube voltage according to preset imaging conditions (imaging form (imaging of still image, imaging of moving image), tube voltage, tube electric current, irradiating time (mAs value), frame rate when imaging the radiation moving image, maximum number of images, etc.).

When the voltage from the high voltage generator is applied, the vacuum tube generates radiation (for example, X-rays) in a dose according to the applied voltage.

The generating apparatus 1 can be fixed in an imaging room or can be configured to be portable on a diagnosis car with the console 5, etc.

For example, when the operation table 4 is operated, the generating apparatus 1 according to the present embodiment generates the radiation in a manner according to the set imaging conditions.

For example, when the set imaging form is imaging of a still image (herein after, still image imaging), the generating apparatus 1 generates the radiation in a predetermined radiation dose only once for a predetermined amount of time.

When the set imaging form is imaging of a radiation moving image including a plurality of frames (hereinafter referred to as moving image imaging), the generating apparatus 1 repeats at a predetermined cycle and a predetermined number of times a pulsed radiation shorter than the still image imaging in a predetermined radiation dose.

When the moving image imaging is performed, the generating apparatus 1 continues to generate radiation while an irradiation instruction switch is being operated.

Radiation Detector

The detector 2 includes a radiation detector, a scanning driver, a reader, an image generator, a communicator, and the like which are not shown.

In the radiation detector, a plurality of charge accumulators which include a switch element and a radiation calculating element which generates charge according to a received dose of radiation are arranged in a two-dimensional shape (matrix shape) corresponding to each pixel of the image (frame).

The scanning driver controls the on and off of the switch elements.

The reader reads an amount of charge discharged from each charge accumulator as a signal value.

The image generator generates image data of the radiation image from a plurality of read signal values.

The communicator is able to transmit and receive various signals and various data with other apparatuses (generating apparatus 1, analysis apparatus 3, console 5, and the like).

The detector 2 may include a scintillator so that the scintillator converts the irradiated radiation to light with other wave lengths such as visible light and the charge is generated according to the converted light (indirect type). Alternatively, the detector 2 can directly generate charge from the radiation without the scintillator (direct type).

The detector 2 can be fixed in the imaging room or can be configured to be portable.

When a predetermined control signal is received from the console 5 and the operation table 4, and the radiation is irradiated from the generating apparatus 1, the detector 2 generates the radiation image according to the set imaging conditions.

For example, when the set imaging form is the still image imaging, the detector 2 performs the imaging operation (accumulating and discharging of charge, reading of signal values, generating of image data) once.

On the other hand, when the set imaging form is the moving image imaging, the detector 2 repeats the imaging operation a predetermined number of times at a predetermined cycle.

That is, the detector 2 includes the function as the moving image generator.

Then, the detector 2 transmits the image data of the generated radiation image (still image, moving image) to the analysis apparatus 3, the console 5, a higher system, or the like wired or wireless through the communicator.

When the dynamic imaging is performed, the detector 2 can generate the frame each time the input timing signal is turned on. Alternatively, after the signal as the trigger of starting the imaging is received once, the detector can repeatedly generate the radiation image a predetermined number of times at its own predetermined cycle.

Dynamic Analysis Apparatus

The analysis apparatus 3 includes a PC, a portable terminal, or a dedicated apparatus.

Based on the radiation moving image obtained from the detector 2, the analysis apparatus 3 analyzes the dynamic state of the chest portion of the subject.

Details of the dynamic analysis apparatus 3 are described later.

Operation Table 4

The operation table 4 includes an irradiation instruction switch which can be operated by the user.

The operation table 4 includes a function in which, when the irradiation instruction switch is operated, at least one of the apparatuses among the generating apparatus 1 and the detector 2 is instructed to start operation.

The operation table 4 according to the present embodiment transmits a signal to instruct the start of operation to both the generating apparatus 1 and the detector 2.

The operation table 4 can be formed as one with the generating apparatus 1 and the console 5.

Console

The console 5 includes a PC, a portable terminal or a dedicated apparatus.

Based on the imaging order information obtained from other systems (HIS, RIS, etc.) and operation performed by the user, the console 5 can set the various imaging conditions (tube voltage, tube electric current, irradiating time (mAs value), imaging site, imaging direction, etc.) in at least one of the generating apparatus 1 and the detector 2.

The set imaging conditions can be displayed on the display provided in the console 5 according to the present embodiment.

FIG. 1 shows a system 100 provided with a console 5 different from the analysis apparatus 3, but the console 5 can be formed as one with the analysis apparatus 3.

Notification Apparatus

The notification apparatus 6 is a notification unit and notifies various information to the subject when the subject undergoes the respiratory examination.

The notification apparatus 6 includes the speaker, the display apparatus, the lamp, and the actuator.

Various notifications include, for example, instructions for the next operation (for example, breathe in, breathe out, hold breath, etc.).

When a measurement apparatus which measures the amount of air breathed out or breathed in by the subject is provided in the system 100, or the analysis apparatus 3 performs the later-described diagnosis supporting process in real time, based on the control signal from the measurement apparatus and the analysis apparatus 3, the notification apparatus 6 can notify the state of breathing out or breathing in the air (degree of breathing out or breathing in compared to the quantitative amount), or imaging result (whether imaging succeeded).

The notification apparatus 6 does not have to be connected directly to the analysis apparatus 3 and can be connected to the console 5 through the communication network N.

The notification apparatus 6 does not have to be an independent apparatus and can be formed as one with the analysis apparatus 3 and console 5.

(Operation of Diagnosis Supporting System)

According to the system 100 as described above, the vacuum tube of the generating apparatus 1 and the detector 2 are positioned opposed to each other with a space in between. The radiation is irradiated from the vacuum tube to the specific site (for example, chest portion) of the subject positioned between the above, and the radiation image of the subject is imaged.

When the subject is imaged in a still state, the irradiating of the radiation and the generating of the radiation image is performed only once in one imaging operation (pressing of the irradiating instruction switch).

When the dynamic state of the subject is imaged, the irradiation of pulsed radiation and the generating of the frame is repeated a plurality of times within a short amount of time in one imaging operation.

Then, the radiation moving image generated by the detector 2 is transmitted to the analysis apparatus 3, and the analysis apparatus 3 analyzes the dynamic state of the subject based on the radiation moving image.

(Analysis Target and Examination Method for Diagnosis Supporting System)

The generating apparatus 1 and detector 2 included in the system 100 is able to image various sites of the subject.

However, the system 100 is for analyzing the dynamic state of the chest portion of the subject based on the radiation moving image in which the chest portion of the subject when the subject is breathing is shown.

Specifically, the system 100 according to the present embodiment analyzes the dynamic state of the chest portion when the predetermined amount of air is breathed out or breathed in.

Therefore, according to the respiratory examination using the system 100, the generating apparatus 1 and the detector 2 are used to image the chest portion of the subject when the predetermined amount of air is breathed out or breathed in.

The above "predetermined amount" is determined according to the subject.

Specifically, the amount is specifically determined as 200 ml, 500 ml, 1000 ml for example, and the above is determined based on the age of the subject, whether before or after the operation, case history, state of rehabilitation, result of diagnosis, and the like.

The above numeric values are merely examples, and the predetermined amount can be suitably set. Preferably, the value is set in a range which does not exceed a limit amount for subjects after the operation or undergoing rehabilitation.

Examples of the method to breathe out or breathe in a predetermined amount of air are described below, and a plurality of methods shown below can be combined.

Place a bag or a container including a predetermined amount of air against the mouth of the subject and allow the subject to breathe in.

Measure the total amount of air to be breathed out or breathed in by the subject and make the subject stop breathing out or breathing in when the total amount reaches the predetermined amount.

While the flow rate and the pressure of the air breathed out or breathed in by the subject is measured, calculate the total amount of air breathed out or breathed in by the subject based on the above values, and make the subject stop breathing out or breathing in when the total amount reaches the predetermined amount.

Preferably, when the predetermined amount of air is breathed out or breathed in, the nose is pinched and the ears are plugged so that air does not leak out.

When the predetermined amount of air is breathed out or breathed in, the above may be performed only once in one respiratory examination or the above can be performed two or more times.

According to the present embodiment, in the respiratory examination in which the predetermined amount of air is breathed out or breathed in two or more times, the chest portion is imaged when a first predetermined amount of air (for example, 200 ml) is breathed out or breathed in and after the state of the breath is returned (if it is after breathing in, then after breathing out, if it is after breathing out, then after breathing in), the chest portion is imaged when a second predetermined amount of air (for example, 500 ml) different from the first predetermined amount is breathed out or breathed in.

When the maximum expiratory volume and the maximum inspiratory volume of the subject is known in advance (for example, measured before the operation), the predetermined amount does not have to be differed, and the predetermined amount can be set to a multiple of the amount 1/N of the maximum expiratory amount or the maximum inspiratory amount of the subject. For example, when the maximum amount is 1200 ml, and N is 3, the amount may be 400 ml (⅓), 800 ml (⅔) and 1200 ml.

The detector 2 generates a first radiation moving image in which the chest portion is shown when a first predetermined amount of air is breathed out or breathed in and a second radiation moving image in which the chest portion is shown when a second amount of air different from the first predetermined amount is breathed out or breathed in.

After the chest portion is imaged when breathing out or breathing in the second predetermined amount of air, the chest portion can be imaged again when breathing out or breathing in a third predetermined amount (for example, 1000 ml) different from the first and second predetermined amount and so on to a M-th predetermined amount as necessary.

The first radiation moving image to an n-th radiation moving image can be made as one (after the imaging of the operation of breathing out or breathing in the n-th predetermined amount of air, the imaging of the operation of breathing out or breathing in a n+1-th predetermined amount of air can be imaged without stopping the operation of the generating apparatus 1 and the detector 2).

As described above, the analysis target and the examination method for the system 100 is described, but in addition to analyzing the dynamic state of the chest portion, the system 100 may also be able to analyze the dynamic state of the portion other than the chest portion.

[2. Details of Dynamic Analysis Apparatus] Next, details of the analysis apparatus 3 provided in the system 100 is described in detail.

Figure 2:
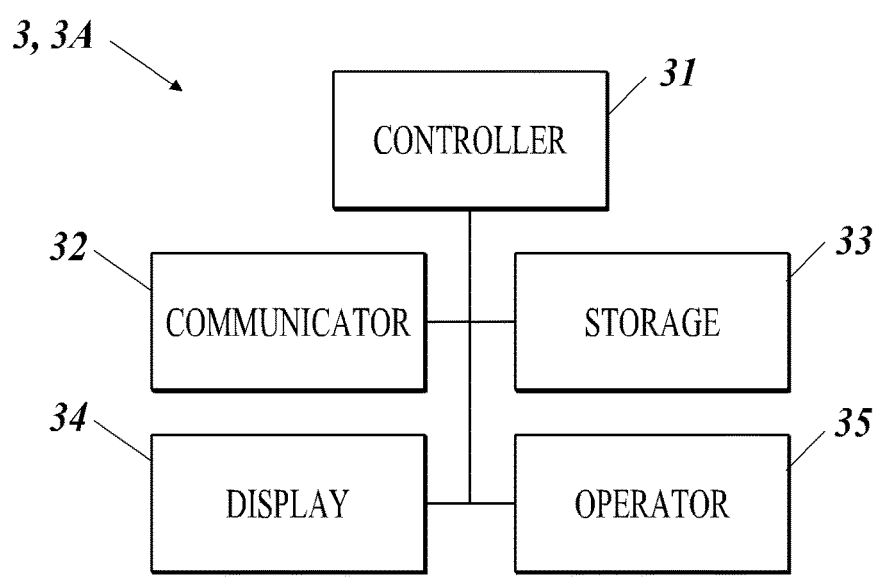
FIG. 2 is a block diagram showing a dynamic analysis apparatus provided in a diagnosis supporting system as shown in FIG. 1.
Figure 3:
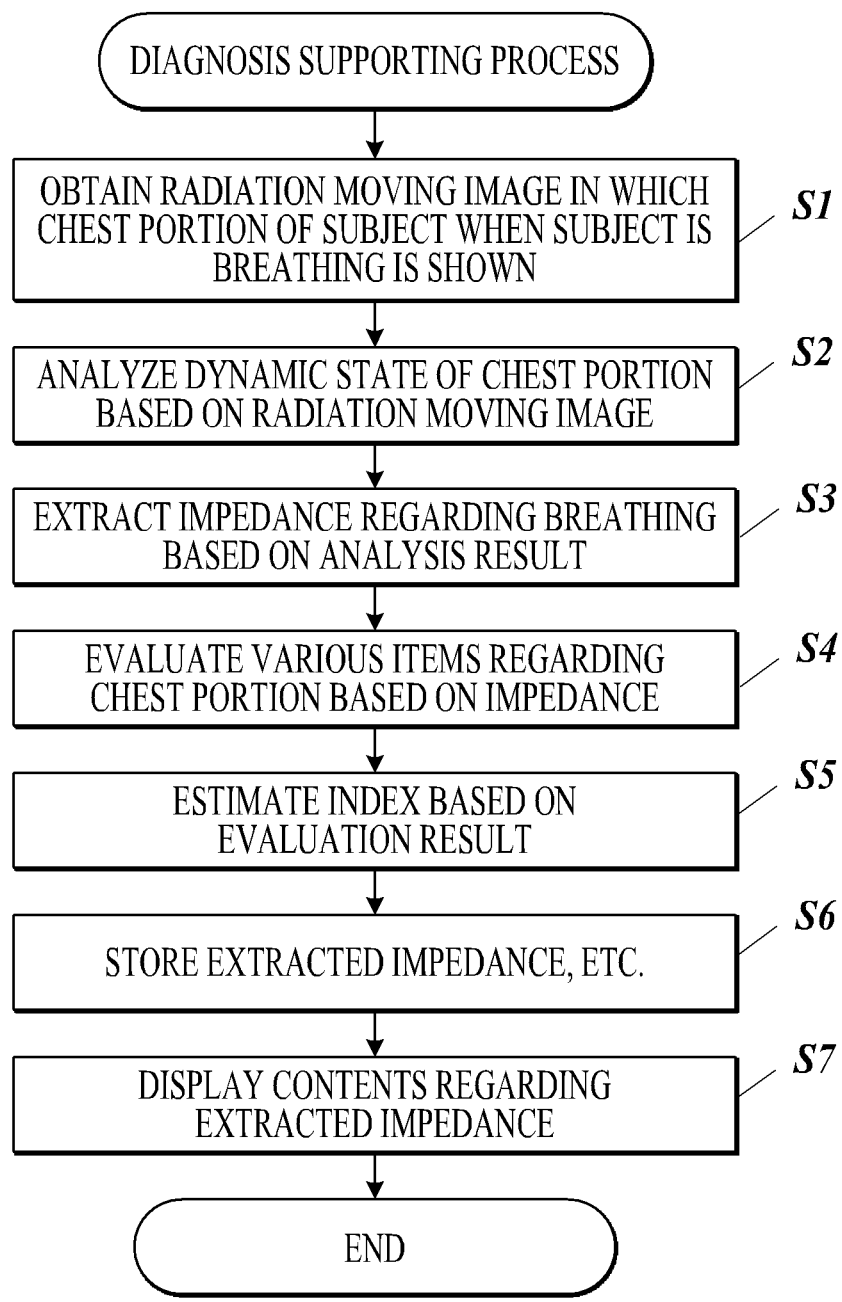
FIG. 3 is a flowchart showing a flow of a diagnosis supporting process executed by a dynamic analysis apparatus as shown in FIG. 3.

FIG. 2 is a block diagram showing the analysis apparatus 3, and FIG. 3 is a flowchart showing a flow of the diagnosis supporting process executed by the analysis apparatus 3.

The reference numeral 3A shown in FIG. 2 is that of the later described second embodiment.

(Configuration of Dynamic Apparatus)

As shown in FIG. 2, the analysis apparatus 3 includes a controller 31, a communicator 32, and a storage 33.

The analysis apparatus 3 according to the present embodiment further includes a display 34 and an operator 35.

The controller 31 includes a CPU (Central Processing Unit), a RAM (Random Access Memory) and the like.

The CPU of the controller 31 reads the various programs stored in the storage 33, deploys the program in the RAM, executes various processes according to the deployed program and centrally controls the operation of the units in the analysis apparatus 3.

The communicator 32 includes a wired communication module or a wireless communication module. The communicator 32 is able to transmit and receive various signals and various data wired or wireless with other apparatuses (generating apparatus 1, detector 2, console 5, etc.) connected through the communication network N.

The storage 33 includes a nonvolatile semiconductor memory, a hard disk, or the like.

The storage 33 stores programs with which the controller 31 executes various processes and parameters necessary to execute the programs.

The storage 33 according to the present embodiment is able to store image data of the radiation image (still image and moving image).

The analysis apparatus 3 stores the image data of the radiation image in the data storage which is not shown provided independent from the storage 33.

The display 34 includes a monitor such as a LCD (Liquid Crystal Display), CRT (Cathode Ray Tube), etc. According to the instruction of the display signal input from the controller 31, various images and various information are displayed.

The operator 35 includes a keyboard which includes a cursor key, a numeric input key, and various function keys, a pointing device such as a mouse, a touch panel layered on the surface of the display 34 and the like. The operator 35 can be operated by the user.

The operator 35 outputs the control signal based on the operation by the operator to the controller 31.

(Operation of the Dynamic Analysis Apparatus)

When the predetermined conditions are satisfied (for example, the operation table 4 is operated, the detector 2 starts generating the radiation moving image (frame), the detector 2 starts transmitting the radiation moving image (frame), the user performs a predetermined operation on the operator 35 or the operator of other apparatuses), the controller 31 of the analysis apparatus 3 executes the diagnosis supporting process as shown in FIG. 3.

In the diagnosis supporting process, first, the controller 31 executes the obtaining process (step S1).

According to the obtaining process, the controller 31 obtains the radiation moving image in which the chest portion of the subject when the subject is breathing is shown.

According to the obtaining process of the present embodiment, the controller 31 obtains the radiation moving image in which the chest portion of the subject when the subject is breathing at least one cycle is shown.

The controller 31 according to the present embodiment obtains the image data of the radiation moving image by receiving the image data from the detector 2, the controller 5 or other systems through the communicator 32.

When the analysis apparatus 3 includes a reader which reads the storage contents in the storage medium, the controller 31 obtains the radiation moving image by reading the image data from the storage medium.

In the obtaining process, the controller 31 according to the present embodiment obtains the radiation moving image showing the chest portion when the predetermined amount of air is breathed out or breathed in.

In the respiratory examination, when the chest portion is imaged from when the first predetermined amount of air is breathed out or breathed in to when the M-th predetermined amount of air is breathed out or breathed in, the controller 31 obtains the first radiation moving image to the M-th radiation moving image in the obtaining process.

The controller 31 functions as the obtaining unit which executes such obtaining process.

After the radiation moving image is obtained, the controller 31 may execute the process to determine whether the obtained radiation moving image is the radiation moving image imaging the chest portion.

The controller 31 may also start the diagnosis supporting process by the radiation moving image being obtained as the trigger. In this case, the obtaining process does not need to be executed in the diagnosis supporting process.

After the radiation moving image is obtained, the controller 31 executes the analysis process (step S2).

In the analysis process, the controller 31 analyzes the dynamic state of the chest portion of the subject based on the radiation moving image obtained in the obtaining process.

Specifically, the state (for example, density (signal value), area, volume, speed, acceleration, vector, or position, or change amount of the above, more preferably, density, area, or position or the change amount of the above) of the target site (for example, lung field, diaphragm, rib cage, rib, airway, etc.) of the chest portion.

In the analysis process according to the present embodiment, the controller 31 calculates the difference between the signal value (density) of the pixel included in the chest portion in one frame included in the radiation moving image and the signal value of another pixel in the frame before or after the one frame with the same coordinates as the pixel in the one frame.

When the first to M-th radiation moving images are obtained in the above obtaining process, the controller 31 analyzes each of the first radiation moving image to the M-th radiation moving image in the analysis process.

The controller 31 functions as the analysis unit which executes such analysis process.

After the dynamic state of the chest portion is analyzed, the controller 31 performs the extracting process (step S3).

According to the extracting process, the controller 31 extracts impedance regarding breathing based on the analysis result obtained in the analysis process.

Such "impedance" is also a function f(x) output as a result of input of a certain quantitative value x.

In the extracting process, the controller 31 according to the present embodiment may extract as the impedance a function value showing the respiratory function of the lung field when the predetermined amount of air is breathed out or breathed in.

Examples of the "function value" include a total lung capacity, forced expiratory volume in one second or a forced expiratory volume % in one second.

Alternatively, the state of the target site (for example, lung field, diaphragm, rib cage, rib, airway, etc.) of the chest portion after a predetermined amount of air is breathed out or breathed in can be extracted, and the "state of the target site" includes, for example, density (signal value), area, volume, speed, acceleration, vector, or position, or change amount of the above, more preferably, density, area, or position or the change amount of the above.

When the first to M-th radiation moving images are analyzed in the analysis apparatus, in the extracting process, the controller 31 extracts the first function value showing the respiratory function of the lung field when the first predetermined amount of air is breathed out or breathed in based on the analysis result of the first radiation moving image to the M-th function value showing the respiratory function of the lung field when the M-th predetermined amount of air is breathed out or breathed in based on the analysis result of the M-th radiation moving image.

That is, when the plurality of quantitative amounts (air amount) are input, the controller 31 outputs discretely (for each predetermined amount) the plurality of function values corresponding to the above.

The controller 31 functions as the extracting unit which executes the extracting process.

After the function value is extracted, the controller 31 executes the evaluating process (step S4).

In the evaluating process, the controller 31 evaluates each item regarding the chest portion based on impedance (function value) extracted in the extracting unit.

The targets of evaluation are described below.
Operation of lung field
Movement of diaphragm
Change of heart/rib cage ratio and rib cage width
Movement of rib and airway
Degree of blood flow
Amount of air which could not be breathed out completely or breathed in completely (remainder)

When the movement of the lung field is evaluated, for example, the function value when 200 ml of the air is breathed in and the function value when 500 ml of the air is breathed in are compared, and next, the function value when 500 ml of the air is breathed in and the function value when 1000 ml of the air is breathed in are compared. Here, when the quantitative value is relatively small (when it is 200 ml and 500 ml), the difference in the function value often appears largely but when the quantitative value is relatively large (when it is 500 ml and 1000 ml), the difference in the function value may appear small or may appear large depending on the subject.

As described here, by observing the difference such as the area of the lung field and the distribution in the lung field of the signal value when the air is breathed in for a first to M-th predetermined amount (for example, 200 ml, 500 ml, 1000 ml, and so on) the change of the expansion in the lung field when the air is continuously breathed in can be evaluated.

When the degree of blood flow is evaluated, the analysis regarding the blood flow can be further performed from the change in the density.

When the amount of air which could not be breathed out completely or breathed in completely is evaluated, for example, when 1000 ml of air could be breathed in but 2000 ml of air could not be breathed in in the respiratory examination, it is possible to assume that the upper limit of air which can be breathed in by the subject is between the above amounts of air. If it is possible to know the excess amount of air which could not be breathed in when the air is breathed in, it is also possible to assume the upper limit of air that can be breathed in by the subject from such remainder amount. In this case, it is possible to make an evaluation from one function value.

For example, in view of the above respiratory examination, if the upper limit of air is assumed to be 1500 ml, when the subject breathes out 1000 ml of the air in the examination to breath out air, this means 500 ml is the amount of air which cannot be breathed out completely.

After the operation of the target site is evaluated, the controller 31 according to the present embodiment performs an estimating process (step S5).

In this estimating process, the controller 31 estimates the index to diagnose the respiratory function of the subject based on the impedance extracted in the extracting process.

In the diagnosis supporting process according to the present embodiment, in order to perform the evaluating process after the extracting process, in the estimating process according to the present embodiment, the controller 31 estimates the index based on the evaluation result performed in the evaluation process (based on impedance).

Examples of the estimated indexes include the following.
Disease which the subject may carry
Degree of normal/abnormal in respiratory function
Item of lung volume fraction When the degree of normal/abnormal in the respiratory function is estimated, the index obtained by performing the respiratory function on the subject and the index obtained by performing the respiratory examination on a healthy person are compared, and the estimate is made based on the degree of the difference.

Figure 4:
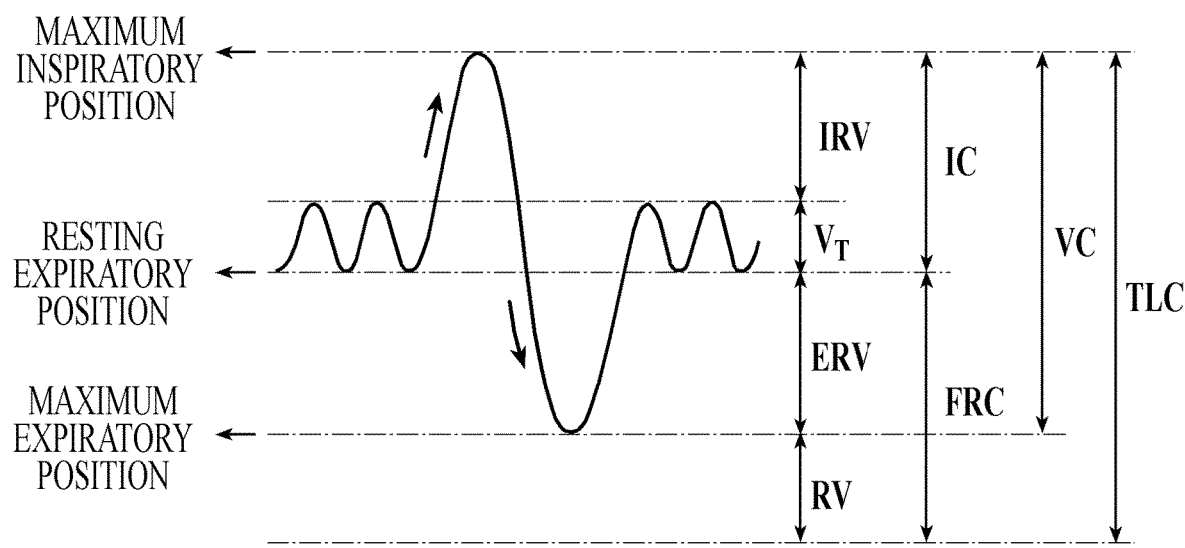
FIG. 4 is a diagram showing a lung volume fraction obtained by the respiratory examination.

When the items of the lung volume fraction are estimated, for example, the evaluation result of the movement of the lung field, that is, the change in the expansion of the lung field (tendency of decrease in speed of expansion) is observed. With this, it is possible to estimate the index showing how much the subject is able to breathe in air (corresponding to maximum inspiratory amount (see FIG. 4)).

Other than the above, by using a similar method, indexes such as vital capacity, % vital capacity, forced vital capacity which are conventionally used for the diagnosis of the respiratory function can be estimated.

The vital capacity is the amount of air when air is breathed in to fill the chest and then all of the air is breathed out.

The % vital capacity is a ratio (%) of the actually measured vital capacity with relation to the estimated vital capacity (reference value) calculated based on the age and sex.

The forced vital capacity is the amount of air when air is breathed in to fill the chest and then the air is breathed out at once with force.

By using a similar method, it is possible to estimate items such as residual volume and total lung capacity which could not be measured by a spirometer.

When the items of the lung volume fraction are estimated, based on the estimated values, it is possible to further estimate the disease which the subject may carry and the degree of normal/abnormal in the respiratory function.

After the index is estimated, the controller 31 according to the present embodiment executes a storing process (step S6).

In the storing process, the controller 31 stores the impedance extracted in the extracting process in the storage.

The storage may be the storage 33 or a storage provided in another apparatus.

The storage process can be executed at any timing after the extracting process is performed.

In the storing process, together with the impedance, the controller 31 may store at least one of the contents regarding impedance (at least one among amount of air breathed out or breathed in, function value, various indexes, estimated result) or a plurality of frames included in the radiation moving image obtained in the obtaining process.

After the impedance is stored, the controller 31 according to the present embodiment performs the display control process (step S7).

In the display control process, the controller 31 displays on the display the contents regarding impedance extracted in the extracting process.

The "contents regarding impedance" includes at least one of amount of air breathed out or breathed in, fraction value, various indexes and estimated result.

The display can be the display 34 or can be a display provided in another apparatus.

The display control process can be performed at any timing after performing the extracting process.

The controller 31 can display the radiation moving image together with the contents regarding impedance.

[3. Effect]

As described above, the analysis apparatus 3 and the system 100 including the analysis apparatus 3 according to the present embodiment extract impedance regarding breathing based on the analysis result of the dynamic state of the chest portion, that is, a function value (output) corresponding to the expiration or inspiration of the predetermined amount (quantitative input).

That is, unlike the conventional measures, the analysis apparatus 3 and the system 100 do not obtain the amount of expiration or inspiration in which the upper limit is not clear. The index based on the function value according to the predetermined amount of expiration or inspiration is obtained. Therefore, the index with high reliability can be obtained.

As a result, according to the analysis apparatus 3 and the system 100 including the analysis apparatus 3 according to the present embodiment, the index to diagnose the respiratory function can be obtained without the subject performing the forced breathing.

Since the subject does not have to perform forced breathing, there is no need for the technician to perform intervention to the subject such as to urge more effort to the subject. As a result, the burden of the technician and the mental and physical pain the subject goes through can be reduced.

Since the index can be performed with breathing in an amount which is not forced, the subject is able to undergo the respiratory examination even soon after the operation.

By carefully observing the respiratory examination of the subjects, and by using indexes estimated by new methods, the diagnosis more suitable for the state of the subject can be performed.

According to the analysis apparatus 3 and the system 100 according to the present embodiment, there is a possibility that the items which cannot be measured in the spirometer such as the residual volume and total lung capacity can be estimated.

Second Embodiment

Next, the second embodiment according to the present invention is described.

Here, the configuration the same as the first embodiment is described with the same reference numeral and the description is referred.

(Analysis Target and Examination Method of Diagnosis Supporting System)

The analysis target is different from the first embodiment in the respiratory function diagnosis supporting system (hereinafter referred to as system 100A) according to the second embodiment.

Therefore, the way the air is breathed out or breathed in when the moving image imaging is performed is different in the respiratory examination using the system 100A according to the present embodiment.

In the respiratory examination according to the present embodiment, the chest portion of the subject is imaged when the subject is breathing out or breathing in the air in a first to M-th predetermined amount within one second.

(Operation of Dynamic Analysis Apparatus)

Some of the processes executed in the diagnosis supporting process is different from the first embodiment in the dynamic analysis apparatus (hereinafter referred to as analysis apparatus 3A) according to the second embodiment.

Specifically, when the movement of the lung field is evaluated in the evaluation process, the controller 31 of the analysis apparatus 3A compares the function value when 200 ml of air is breathed out in one second, the function value when 500 ml of air is breathed out, and the function value when 1000 ml of air is breathed out.

When the change amount of the lung field area is the function value, comparison is performed as follows, for example, the change rate of the lung field area is large at 200 ml but the change rate gradually becomes smaller as the amount of air increases to 500 ml and 1000 ml.

When the change amount of the position of the rib cage is the function value, comparison is performed as follows, for example, the movement of the rib cage shows a smooth expansion at 200 ml but the movement shows small trembling as the amount of air increases to 500 ml and 1000 ml.

As described above, by observing the difference of the area of the lung field and the lung field distribution of the signal value when the air is breathed out from the first predetermined amount to the M-th predetermined amount (for example, 200 ml, 500 ml, 1000 ml, and so on), the change of the contraction of the lung field when the air is breathed out in one second can be evaluated.

In the estimating process, by observing the evaluation result of the movement of the lung field, that is, the change in the contraction of the lung field, it is possible to estimate the index showing the ability of how much air the subject can breathe out in one second (corresponding to forced expiratory volume in one second).

If the index corresponding to the forced expiratory volume in one second can be estimated, the forced expiratory volume % in one second (ratio of forced expiratory volume in one second with relation to forced vital capacity) can be calculated.

(Effect)

Similar to the analysis apparatus 3 and the system 100 according to the first embodiment, according to the analysis apparatus 3A and the system 100A provided with the analysis apparatus 3A in the present embodiment, the index to diagnose the respiratory function can be obtained without the subject performing forced breathing.

<Others>

Embodiments are described above, but the present invention is not limited to the described embodiments, and various modifications are possible without leaving the scope of the present invention.

For example, according to the above embodiment, the analysis apparatus 3 extracts impedance regarding breathing based on the radiation moving image which shows the chest portion of the subject when the subject breathes. Alternatively, the impedance can be extracted in the respiratory examination by repeatedly imaging the still image of the chest portion of the subject a plurality of times while the subject breathes out or breathes in a predetermined amount of air and obtaining the difference of the signal values of the pixels in the still images.

According to the above description, as the computer readable medium including the program to execute the present embodiment, a hard disk or a nonvolatile semiconductor memory is used, but examples are not limited to the above. A portable storage medium such as a CD-ROM can be used as the computer-readable medium. Carrier waves can be applied as the media to provide the data of the program of the above embodiment through communication lines.

Although embodiments of the present invention have been described and illustrated in detail, the disclosed embodiments are made for purposes of illustration and example only and not limitation. The scope of the present invention should be interpreted by terms of the appended claims.

What is claimed is:

1. A non-transitory computer-readable storage medium storing a program causing a computer to perform:

obtaining a radiation moving image in which a chest portion of a subject when the subject breathes is shown;

analyzing a dynamic state of the chest portion based on the radiation moving image obtained in the obtaining; and extracting impedance regarding breathing based on an analysis result obtained in the analyzing, wherein in the analyzing, a difference is calculated between a signal value of a pixel included in the chest portion in one frame included in the radiation moving image and a signal value of another pixel in another frame before or after the one frame wherein the another pixel has the same coordinates as the pixel in the one frame.

2. The storage medium according to claim 1, wherein, in the obtaining, the radiation moving image in which the chest portion is shown when a predetermined amount of air is breathed out or breathed in is obtained; and in the extracting, a total lung capacity, a forced expiratory volume in one second or a forced expiratory volume % in one second which is a function value showing a respiratory function of a lung field when a predetermined amount of air is breathed out or breathed in is extracted as the impedance.

3. The storage medium according to claim 2, wherein, in the obtaining, a first radiation moving image in which the chest portion is shown when a first predetermined amount of air is breathed out or breathed in, and a second radiation moving image in which the chest portion is shown when a second predetermined amount of air different from the first predetermined amount of air is breathed out or breathed in are obtained;

in the analyzing, the first radiation moving image and the second radiation moving image are analyzed; and in the extracting, a first function value showing the respiratory function of the lung field when the first predetermined amount of air is breathed out or breathed in is extracted based on the analysis result of the first radiation moving image, and a second function value showing the respiratory function of the lung field when the second predetermined amount of air is breathed out or breathed in is extracted based on the analysis result of the second radiation moving image.

4. The storage medium according to claim 1, wherein in the extracting, the program further causing the computer to perform estimating of an index to diagnose the respiratory function of the subject based on the extracted impedance.

5. The storage medium according to claim 4, wherein in the estimating, at least one of a residual volume and a total lung capacity is estimated as the index.

6. The storage medium according to claim 1, wherein in the obtaining, the radiation moving image in which the chest portion of the subject when at least one cycle of breathing is performed is shown is obtained.

7. The storage medium according to claim 1, wherein in the extracting, the program further causing the computer to perform displaying of contents regarding the extracted impedance on a display.

8. The storage medium according to claim 1, wherein, in the extracting, the program further causing the computer to perform storing of the extracted impedance in a storage.

9. A non-transitory computer-readable storage medium storing a program causing a computer to perform:

obtaining of a radiation moving image in which a chest portion is shown when a predetermined amount of air is breathed out or breathed in;

analyzing a dynamic state of the chest portion based on the obtained radiation moving image;

based on an analysis result obtained in the analyzing, extracting a density, area or position of a target site included in the chest portion or a change amount of the density, a change amount of the area or a change amount of the position.

10. A dynamic analysis apparatus comprising:
a hardware processor,
wherein the hardware processor is configured to perform,
obtaining a radiation moving image in which a chest portion of a subject when the subject breathes is shown,
analyzing a dynamic state of the chest portion based on the radiation moving image obtained in the obtaining, and
extracting impedance regarding breathing based on an analysis result obtained in the analyzing,
wherein in the analyzing, a difference is calculated between a signal value of a pixel included in the chest portion in one frame included in the radiation moving image and a signal value of another pixel in another frame before or after the one frame wherein the another pixel has the same coordinates as the pixel in the one frame.

11. A diagnosis supporting system comprising:
a detector which generates a radiation moving image in which a chest portion of a subject when the subject breathes is imaged; and
a dynamic analysis apparatus,
wherein the dynamic analysis apparatus is configured to perform,
analyzing a dynamic state of the chest portion based on the radiation moving image generated by the detector; and
extracting impedance regarding breathing based on an analysis result obtained in the analyzing,
wherein in the analyzing, a difference is calculated between a signal value of a pixel included in the chest portion in one frame included in the radiation moving image and a signal value of another pixel in another frame before or after the one frame wherein the another pixel has the same coordinates as the pixel in the one frame.

12. The diagnosis supporting system according to claim 11, further comprising a notification apparatus which notifies various information to the subject when the subject undergoes a respiratory examination.

13. A non-transitory computer-readable storage medium storing a program causing a computer to perform:
obtaining a radiation moving image in which a chest portion of a subject when the subject breathes is shown;
analyzing a dynamic state of the chest portion based on the radiation moving image obtained in the obtaining; and
extracting impedance regarding breathing based on an analysis result obtained in the analyzing, wherein,
in the obtaining, a first radiation moving image in which the chest portion is shown when a first predetermined amount of air is breathed out or breathed in, and a second radiation moving image in which the chest portion is shown when a second predetermined amount of air different from the first predetermined amount of air is breathed out or breathed in are obtained;
in the analyzing, the first radiation moving image and the second radiation moving image are analyzed;
in the extracting, a first function value showing the respiratory function of the lung field when the first predetermined amount of air is breathed out or breathed in is extracted based on the analysis result of the first radiation moving image, and a second function value showing the respiratory function of the lung field when the second predetermined amount of air is breathed out or breathed in is extracted based on the analysis result of the second radiation moving image, each of the first function value and the second function value being a total lung capacity, a forced expiratory volume in one second or a forced expiratory volume % in one second.

* * * * *